United States Patent [19]

Brennan

[11] 4,103,087
[45] Jul. 25, 1978

[54] PRODUCTION OF DI-(N,N-DISUBSTITUTED AMINO) ALKANES

[75] Inventor: Michael E. Brennan, Austin, Tex.

[73] Assignee: Texaco Development Corporation, New York, N.Y.

[21] Appl. No.: 783,594

[22] Filed: Apr. 1, 1977

[51] Int. Cl.$^2$ .............. C07D 295/12; C07D 295/00; C07D 265/30

[52] U.S. Cl. .................................. 544/78; 544/87; 544/121; 544/141; 544/162; 544/165; 544/170; 260/326.85; 260/563 R; 260/583 P; 544/357; 544/372; 544/402; 544/398

[58] Field of Search ............... 260/246 B, 247.5 R; 544/78, 121, 141

[56] References Cited

U.S. PATENT DOCUMENTS

| 3,121,115 | 2/1964 | Meuly | 260/570.5 |
| 3,843,648 | 10/1974 | Bechara | 260/247.5 R |

Primary Examiner—Jose Tovar
Attorney, Agent, or Firm—Carl G. Ries; Thomas H. Whaley; James L. Bailey

[57] ABSTRACT

An improved process is disclosed for selectively producing a di-(N,N-disubstituted amino) alkane compound which includes contacting an (N,N-disubstituted) amino alkanol compound with an (N,N-disubstituted) amine compound in the presence of a catalytically effective amount of an aluminum phosphate catalyst at a temperature of from about 240° C to 320° C under a pressure sufficient to maintain the mixture substantially in liquid phase and recovering from the resultant reaction mixture the di-(N,N-disubstituted amino) alkane compound.

According to a preferred embodiment, N-(2-hydroxyethyl) morpholine is contacted with morpholine in the presence of a catalytically effective amount of a heterogeneous aluminum phosphate catalyst at temperatures of from about 260° C to about 300° C in liquid phase to selectively produce the corresponding N,N'-dimorpholino ethane (DMORE).

13 Claims, No Drawings

PRODUCTION OF DI-(N,N-DISUBSTITUTED AMINO) ALKANES

BACKGROUND OF THE INVENTION

1. Field of the Invention

The instant invention generally relates to an improved process for producing di-(N,N-disubstituted amino) alkane compounds directly from a tertiary amino alkanol and a secondary amine compound; and more particularly, to an improved selective liquid phase process for directly producing a di-(N,N-disubstituted amino) alkane compound in the presence of certain specific catalytically effective substances.

2. Prior Art

Di-(N,N-disubstituted amino) alkanes are generally well-known compounds. These compounds have established utility as polyurethane catalysts, epoxy curing agents and as intermediates in the preparation of corrosion inhibitors, pharmaceuticals, emulsifiers, textile chemicals, rubber chemicals and the like. For example see Doyle, E. No., *The Development and Use of Poly Urethane Products*, McGraw-Hill Book Co., 1971, page 69. A specific class of these compounds, being the N,N'-dimorpholino alkanes, is an especially preferred polyurethane catalyst. Generally, this class is useful in catalyzing urethane systems including the C-lower alkyl substituted N,N'-dimorpholino alkane compounds wherein one or both of the morpholine moieties contain C-(substituted) lower alkyl radicals on one or more of the carbon atoms and/or wherein the alkane moiety is either a branched or straight chain divalent radical containing from 1 to about 10 carbon atoms. Corresponding compounds containing a single morpholino moiety, such as 4-(2-dimethylaminoethyl)morpholine also are useful as polyurethane catalysts. The di-(N,N-disubstituted amino) alkanes are well-known as shown in U.S. Pat. No. 3,121,115.

Di-(N,N-disubstituted amino) alkanes have generally been prepared by methods involving halogenated reactants or intermediates. For example, in one method, N-(2-chloroethyl) morpholine is reacted with morpholine. Such methods of preparation are unsatisfactory in that the halogenated reactants are not readily available, and the methods involve caustic neutralization of the product and the concomitant disposal of polluting by-products, such as the alkali halide salts. Ditertiary amino alkanes have been prepared non-catalytically notably by heating the tertiary amino alkanol and the secondary amine with an acid condensing agent in a quantity such that the acid is present in at least the molar equivalent of the amino alkanol.

In addition, there are procedures described in the literature for preparing N-alkylated amines in the presence of various catalysts. For example, it is known that metal phosphates catalyze the alkylation of amines, such as morpholine, with an alkyleneimine. For example, see U.S. Pat. No. 3,527,757. Additionally, it is disclosed in U.S. Pat. No. 3,843,648 that N-aminoalkylated morpholines are produced by the condensation of N,N-dimethylaminoethanol and morpholine in vapor phase in the presence of $AlPO_4$ catalyst or a silica-alumina cracking catalyst at temperatures of 200° C to 400° C. However, as disclosed in this reference, the selectivities to the desired product make the process particularly commercially unattractive. This is especially true when the conversion of the limiting reactant approaches 100%.

Additionally, it has been disclosed that certain phosphoric acid compounds are effective as catalysts in promoting condensation reactions between several types of amines and aminoalkanols which are carried out under relatively mild liquid phase processing conditions. For example, U.S. Pat. No. 3,121,115 to Meuly teaches a process for aminoalkylating certain amines having a replaceable amino hydrogen, particularly aromatic primary and secondary amines, which includes heating the amine compound with a N-tertiary aminoalkanol at from 150° C to 250° C in liquid phase with continuous water removal in the presence of a phosphoric acid compound such as aqueous or anhydrous orthophosphoric acid, phosphorus pentoxide or an alkyl phosphoric acid. Although this reference discloses homogeneous phosphorus dehydration catalysts, the selectivities, conversions and reaction times teach the process as particularly undesirable for commercial processes. Further use of the homogeneous catalyst requires separation of catalyst from he homogeneous product. The disclosed process requires long reaction times.

Therefore, a process having high selectivity at high conversion rates would be commercially advantageous. Unexpectedly, such a process has been inadvertently discovered. Importantly, the discovered process does not share the drawbacks of vapor phase or those associated with homogeneous catalyst recovery. Specifically, di-(N,N-disubstituted amino) alkanes can be produced with unexpectedly high selectivity in liquid phase at temperatures above about 250° C in the presence of a heterogeneous alumina phosphate catalyst. Surprisingly, it has been found that the rather severe reaction conditions of the instant process facilitate product formation without the expected decomposition and formation of excessive by-products. Thus, selectivity is unexpected and surprising while activity is comparable to other well known processes. The limiting reactant can be recycled to accomplish a substantially 100% yield of the desired product, a result heretofore taught in the art as unachievable. The instant process does not require an expensive neutralization step nor is it attended by vapor phase reaction deficiencies such as vaporizing the reactants, low conversion rates, low selectivities, catalyst deactivation and the like. The catalyst is also heterogeneous, eliminating costly separation problems.

SUMMARY OF THE INVENTION

According to the broad aspect of the instant invention, an amine having one labile hydrogen is aminoalkylated with a tertiary aminoalkanol in the presence of a catalytically effective amount of heterogeneous aluminum phosphate at temperatures of from about 240° C to about 320° C at pressures sufficient to maintain the reactants and products in liquid phase.

DESCRIPTION OF THE PREFERRED EMBODIMENTS

In accordance with a preferred embodiment an N-(hydroxyalkyl)morpholine compound and a morpholine compound are continuously fed into a fixed bed reactor at space velocities of from 0.2 to about 2.0 g/ml catalyst/hr at temperatures of from about 240° C to 300° C. A fixed bed of aluminum phosphate is employed containing about 25 wt. % phosphorus and having a surface area of about 33 $m^2/g$. The reactor pressure is maintained at about 200–500 psig. The liquid effluent is collected and purified according to standard distillation techniques.

In accordance with the inventive process, the di-(N,N-disubstituted amino) alkane compounds produced are a result of the bimolecular dehydration of an N,N-disubstituted aminoalkanol, such as an N-(hydroxyalkyl)morpholine and an N,N-disubstituted amine such as morpholine. Thus, by varying the N,N-disubstituted moieties of the reactants utilized, one may achieve, for example the corresponding bis-(N,N-disubstituted amino) alkane compound. Additionally, by varying the chain length or the branched configuration of the alkylene moiety of the N,N-disubstituted aminoalkanol reactant, one may achieve di-(N,N-disubstituted amino)alkanes having the corresponding alkylene moiety.

The N,N-(disubstituted)aminoalkanols useful in the practice of this invention can be generally described as tertiary aminoalkanols wherein the hydroxy moiety is either primary or secondary. These compounds can be depicted by the formula

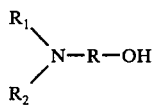

wherein R is an alkylene radical of from 2 to about 10 carbon atoms and more preferably 2 to about 4. R can either be of a straight, i.e., normal or branched chain configuration, but preferably the normal chain contains no more than about 4 carbon atoms and more preferably 2 carbon atoms. R is most preferably an ethylene, 1,2-propylene, or 1,2-butylene radical. $R_1$ and $R_2$, independently, are straight or branched chain alkyl radicals of from 1 to about 18 carbon atoms, preferably from 1 to about 10 carbon atoms, and most preferably from 1 to about 4; or $R_1$ and $R_2$, taken together with the nitrogen atom to which each is attached, can form a heterocyclic ring such as morpholino, C-(alkyl substituted)morpholino, piperazino, C-(alkyl substituted)piperazino, pyrrolidino, and the like.

It should be noted that, in accordance with the useful aminoalkanol alkylating agents, the secondary amino radical, i.e., that moiety to which the alkanol is attached, has the character of an aliphatic or cycloaliphatic hydrocarbon amino radical. This amino radical can consist of one or two hydrocarbon radicals joined to the amino nitrogen through saturated carbon atoms and includes such radicals wherein the two carbons attached to the nitrogen are part of the same divalent hydrocarbon radical, which, together with the nitrogen, constitutes a cyclic secondary amine radical. It should further be realized that it is not critical that the radical appended to the amino nitrogen be completely hydrocarbon. They may be substituted radicals such as oxa-, thia-, and aza- analogs of the corresponding hydrocarbons provided that the nitrogen with such attended radicals has the character of a basic aliphatic or cycloaliphatic amino nitrogen moiety.

Examples of suitable such compounds include N,N-dimethylaminoethanol; N,N-diethylaminopropanol; N-methyl, N-ethylamino-1,2-butanol; N-(2-hydroxyethyl) morpholine, N-2-hydroxypropyl piperazine; N-hexyl, N-pentylamino-n-butanol; N,N-didecylamino n-heptanol; N-butyl N-propylamino-2-butyl heptanol and the like. The foregoing are representative examples only and the inventive concept specifically covers each and every homologous compound within the previously described limits.

In accordance with one embodiment, $R_1$ and $R_2$, in the above formula, taken together with the nitrogen atom to which each is attached, form a heterocyclic ring which can be C-alkyl substituted. Preferably such compounds are N-(hydroxyalkyl)morpholines depicted by the formula

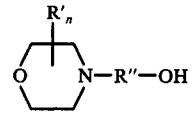

wherein R" is a straight chain or a branched alkyl radical of from 2 to about 4 carbon atoms, R' is a lower alkyl radical of from 1 to about 4 carbon atoms such as methyl, ethyl and the like and n is an integer from 0 to 4. Illustrative of the N-(hydroxyalkyl)morpholines are N-(3-hydroxybutyl)morpholine, N-(2-hydroxypropyl)morpholine, N-(2-hydroxyethyl)-2-methylmorpholine, N-(2-hydroxyethyl)-2,5-dimethylmorpholine, N-(2-hydroxypropyl-2,3,5,6-tetrapropylmorpholine and the like. Preferred N-(hydroxyalkyl)morpholines are of the above formula wherein R is an n-alkyl radical of from 2 to about 3 carbon atoms. Especially preferred are N-(hydroxyalkyl)morpholines of the above formula wherein R is an alkyl radical of from 2 to about 3 carbon atoms, and n is 0. Most preferred is N-(2-hydroxyethyl)-morpholine.

It will be realized by the skilled artisan that the N-substituted piperazine compounds, pyrrolidine compounds, i.e., other 5 and 6 membered heterocyclic basic nitrogen compounds may be utilized to substantially the same extent and in the same manner as the previously described morpholine compound.

The N,N-(disubstituted)amines which are useful in the practice of this invention can be generally characterized as secondary amines. These compounds can be depicted by the formula

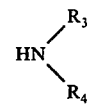

wherein $R_3$ and $R_4$ are as $R_1$ and $R_2$ defined above. Illustrative amines include dimethylamine; diethylamine; dihexylamine; ethylpropylamine; morpholine; 2-methylmorpholine; 2-ethylmorpholine; 2,6-dimethylmorpholine; decyl heptyl amine; dioctylamine; 2,5-dimethyl morpholine; 2,5-dipropyl-3,6-diethylmorpholine and the like. The above list is not meant as exhaustive.

Preferred N,N-(disubstituted)amines in the practice of this invention are those of the above formula wherein $R_3$ and $R_4$, independently, are lower alkyl radicals having from about 2 to about 4 carbon atoms and morpholine or the C-(alkyl substituted)morpholines wherein the C-alkyl substituents are lower alkyl radicals of 1 to about 2 carbon atoms such as methyl, and ethyl radicals.

The catalysts which are useful in practicing the process of this invention are generally characterized as aluminum phosphates having a phosphorus content of from 20 to 30 wt. % based on the weight of the catalyst material, and a surface area of from 20 m$^2$/g to 50 m$^2$/g. The preferred catalyst contains from about 23 to 27 wt.

% with a surface area of 33 m²/g; and, the most preferred contains about 25 wt. %.

The instant catalyst can be characterized as heterogeneous under the conditions of the reaction. Thus, attendant catalyst separation problems encountered in utilizing homogeneous systems are obviated. In fact, it is surprisingly shown that the instant catalyst composition does not tend to leach to an extent found in even prior art aluminum phosphate catalysts. Thus, the instant process is shown further advantageous over other processes. Specifically, one reason for running such reactions in vapor phase is the prevention of prior art catalyst leaching.

The catalyst of the instant process can better be described in terms of its preparation. Hydrated alumina is first dissolved in concentrated phosphoric acid and the metal phosphate is precipitated by addition of a neutralizing amount of aqueous ammonium hydroxide. The precipitate is then isolated and calcined in accordance with standard procedures.

Generally, any hydrated alumina ($Al_2O_3 \cdot 3H_2O$) is useful in forming the catalyst material. Selection of a specific material does not appear critical. Sufficient concentrated phosphoric acid ($H_3PO_4$) is added to dissolve the alumina. Mole ratios of $H_3PO_4/Al_2O_3 \cdot 3H_2O$ in the range of 5.5 to 10 have been found sufficient. A molar ratio of about 6 is preferred. Solubilizing temperatures are utilized which normally are from about 90° to 120° C.

A precipitating amount of a base is then slowly added to precipitate the catalyst material. The base utilized is not particularly critical. The only requirement is that a final pH of about 6 be reacted. Ammonium hydroxide is preferred primrily because of the absence of a second metal ion.

The aluminum phosphate catalysts can be employed in any well known form such as a fine powder or as a pellet. Pelletized catalysts are particularly suitable for continuous processes in which the catalyst may be employed as a fixed bed. The particular physical form in which the catalyst is employed is not critical in the process of this invention.

The amount of catalyst employed in the process of this invention will depend on the particular reactants involved. In batch processes, aluminum phosphate catalysts in an amount of from about 1 to about 20 wt. %, based upon the amount of aminoalkanol present, has been found satisfactory, with an amount of from about 5 to about 10 wt. % being preferred. In a continuous reaction process wherein the catalyst is generally employed as a fixed bed, a weight hourly space velocity (WHSV) of from about 0.1 to about 5.0 g/ml catalyst/hr is satisfactory with a space velocity of from about 0.2 to about 2.0 g/ml catalyst/hr being preferred.

In the process of this invention, one mole of the N,N-(disubstituted)aminoalkanol will react with one mole of the N,N-(disubstituted)amine. However, the process of this invention may be practiced with an excess of either reactant. Generally a ratio of aminoalkanol to amine of from about 1:10 to about 10:1 may be employed. However, it is generally desirable to employ a slight excess of the N,N-(disubstituted)amine in order to minimize the formation of the bis-(N,N-disubstituted aminoalkyl)ether. Therefore, ratios of aminoalkanol to amine of from about 1:1 to about 1:10 are preferred in order to maximize the yield of bis-(N,N-disubstituted amino)alkane. Especially preferred are ratios of aminoalkanol to amine of from about 1:1 to about 1:4.

One especially advantageous aspect of the instant inventive process resides in the fact that the reactants are very selectively converted to the desired product such that the remaining reactants can be recycled without appreciable by-product removal to effect a 100% desired yield in a short number of passes. This not only increases effectiveness of the process, but decreases by-product disposal problems.

The bimolecular dehydration reaction of this invention, as described herein, is carried out substantially in a liquid phase reaction which is conducted at a temperature of from about 240° C to about 320° C. The exact temperature range selected is somewhat empirical and will depend upon the particular reactants employed and the desired conversion levels. It has been found that temperatures in the range of from about 260° C to 300° C are normally sufficient for good yield production of desired bis-(morpholino)alkanes. When N,N'-dimorpholinoethane (DMORE) is produced, temperatures in the range of 270° C to 290° C are most preferred.

The pressure at which the reaction is carried out can be at any pressure sufficient to maintain the reactants substantially in liquid phase. For example, generally, reaction pressures of from about 100 to about 1000 psig have been found satisfactory with 200–500 being preferred. However, there is no incentive to employ reaction pressures higher than is necessary to maintain the reactants and products substantially in the liquid phase. By substantially in the liquid phase is meant the following. As has been discussed previously, water is formed as a co-product of the bimolecular condensation reaction. It has been found advantageous in batch processes to maintain the water content of the reaction system at as low a level as is possible in order to enhance catalytic activity and simultaneously to shift the reaction equilibrium toward the desired product. Therefore, it is desirable to maintain the reaction zone at a pressure such that the water formed in the bimolecular condensation reaction will be removed from the reaction zone as a vapor. It has been found that for typical reaction mixtures wherein morpholine and N-(2-hydroxyethyl)-morpholine are the reactants at temperatures in the range of from about 260° C to about 300° C, the preferred reaction zone pressure is from about 200 to about 500 psig, with pressures of about 275 psig being most preferred.

In practicing the process of this invention a solvent is not required, but may be employed if desired. Whenever a solvent is employed, the solvent should be non-deleterious to the reaction environment and the desired reaction. Examples of suitable solvents include hydrocarbon solvents such as hexane, decane, dodecene, benzene, and the like, and chlorinate aromatic solvents such as chlorobenzene.

The crude reaction product obtained from the process of this invention will comprise the desired bis-(N,N-disubstituted amino)alkane in combination with the coproduct, bis-(N,N-disubstituted aminoalkyl)ether, a small amount of heavy materials and unreacted reactants. In some embodiments of the process of this invention, the catalyst will also be present in the crude reaction mixture. For example, it has been found that the catalyst may be recovered from the crude reaction mixture and recycled for reuse according to the process of this invention. It is generally preferable to wash the recovered catalyst, for example with methanol and/or water, and dry it prior to recycling it for reuse.

The bis-(N,N-disubstituted amino)alkane is recovered from the crude reaction mixture by conventional means, for example distillation, extraction, crystalization and the like. The unreacted N,N-(disubstituted)aminoalkanol and N,N-(disubstituted)amine are recovered and advantageously able of recycle for further conversion to the desired product.

The process of this invention will now be further illustrated in the following examples which are for the purposes of illustration and should not be considered a limitation on the scope of the invention.

EXAMPLE I

In this example, the aluminum phosphate catalyst material used in the instant inventive process was prepared in three steps. In a first step, 67.6 g (0.433 moles) of a hydrated alumina sold by Reynolds Chemical under the designation "RH-31F" (65.25* $Al_2O_3$; 0.13 $Na_2O$; 0.008 $SiO_2$; 0.003 $Fe_2O_3$; 0.02 free water; bulk density 60-80 lb/ft$^3$) and 279.4 g (2.42 moles) of 85% phosphoric acid were charged to a clean, dry 250 ml, round bottom flask. The charged reaction admixture exhibited a delayed exotherm which caused the temperature to rise to about 120° C, yielding a very viscous, homogeneous solution. The resultant hot solution was poured into 750 ml of distilled water with continual stirring to yield a clear, colorless solution having a pH of about 2 to 3.
*Weight percent, dry basis.

In a second step, a 30% aqueous solution of ammonium hydroxide was added to the clear, colorless aqueous solution of step 1, causing a white precipitate to instantaneously form. The ammonium hydroxide addition was continued until no further precipitation was observed. The solids were collected by evacuated filtration, and then washed first with 7, 500 ml aliquots of distilled water and then with 4, 500 ml aliquots of methanol. The resultant solid, which weighed 589 g was dried in a vacuum desiccator (80°-110° C, full pump) for about 16 hours. The weight of the dried solid was about 173 g.

In a third step, the dried solid was divided and one-half of the material was calcined in an oven at 250° C for about 7 hours with a resulting additional 14.8% measured weight loss. The calcined and uncalcined material were analyzed for phosphorus, aluminum and sodium by atomic absorption (AA) spectroscopy and for nitrogen content by the standard Kjeldahl procedure. The analysis showed the following:

|  | Weight % | | | Ppm. |
|---|---|---|---|---|
|  | P | Al | N | Na |
| Uncalcined material | 23.7 | 12.45 | 6.05 | 194 |
| Calcined material | 27.8 | 15.6 | 2.57 | 172 |
| (Calculated theoretical for $AlPO_4$) | 25.4 | 22.1 | — | — |

EXAMPLE II

To a clean, dry 1-liter stirred autoclave were charged 1.0 mole (131.2 g) N-(2-hydroxyethyl)morpholine (HEM), 2.0 moles (174.2 g) morpholine and 13.1 g of an calcined aluminum phosphate catalyst prepared according to a procedure as in Example I. The autoclave was then purged and padded with nitrogen and heated to a temperature of approximately 260° C. The autoclave was maintained at this temperature for 4 hours during which time the reaction pressure ranged from 178 to 195 psig. The contents of the autoclave were then cooled, recovered and subjected to gas-liquid chromatographic analysis. Analysis of the yellow liquid effluent showed that 32.0 wt. % of the HEM and 14.7 wt. % of the morpholine had been converted to products consisting essentially of 1,2-dimorpholinoethane (DMORE) an 2,2'-dimorpholinodiethylether (DMDEE). The selectivity to DMORE was 98.5% and the selectivity to DMDEE was 1.0%, based upon the above conversion.

EXAMPLE III

According to the general procedures of Example II, 1.0 mole (131.2 g) N-(2-hydroxyethyl) morpholine (HEM) and 2.0 moles (174.2 g) morpholine were contacted in the presence of 13.1 g of the aluminum phosphate catalyst of Example I. The reaction mixture was heated to 270° C for 4 hours (260-290 psig). Gas chromatographic analysis (area %) of the recovered product showed that 58.2 wt. % of the HEM and 24.6 wt. % of the morpholine had been converted to products consisting essentially of 1,2-dimorpholinoethane (DMORE) and 2,2'-dimorpholinodiethylether (DMDEE). The selectivity to DMORE was 95.9 wt. % and the selectivity to DMDEE was 1.1 wt. % based on the foregoing conversions.

EXAMPLE IV

According to the general procedures of Example II, 1.0 mole (131.2 g) N-(2-hydroxyethyl) morpholine (HEM) and 2.0 moles (174.2 g) morpholine were contacted in the presence of 13.1 g of the aluminum phosphate catalyst of Example I. The reaction mixture was heated to 280° C for 4 hours (290-450 psig). Gas chromatographic analysis (area %) of the recovered product showed that 63.2 wt % of the HEM and 33.5 wt. % of the morpholine had been converted to products consisting essentially of 1,2-dimorpholinoethane (DMORE) and 2,2'-dimorpholinodiethylether (DMDEE). The selectivity to DMORE was 97.0 wt % and the selectivity to DMDEE was 0.9 wt % based on the foregoing conversions.

EXAMPLE V

This example demonstrates the superiority of the instant process over a similar process using a commercial aluminum phosphate catalyst.

According to the general procedures of Example II, 1.0 mole (131.2 g) N-(2-hydroxyethyl) morpholine (HEM) and 2.0 moles (174.2 g) morpholine were contacted in the presence of 31.2 g of a conventional $AlPO_4$ catalyst on alumina (8.90 wt % P) sold by Girdler Chemical Co., Inc., Louisville, Kentucky 40201 under the designation "Girdler T-1067". The reaction mixture was heated to 260° C for 4 hours at 175 psig. 332 grams liquid effluent were recovered representing 98.6% of theoretical. Gas chromatographic analysis (area %) of the recovered product showed that only 7.9 wt % of the HEM and 4.5 wt. % of the morpholine had been converted. Basis the small amount of converted product, the selectivity to DMORE was 72.0 wt % and the selectivity to DMDEE was 2.0 wt %.

While the invention has been explained in relation to its preferred embodiment, it is to be understood that various modifications thereof will become apparent to those skilled in the art upon reading the specification and is intended to cover such modifications as fall within the scope of the appended claims.

What is claimed is:

1. A process for producing a di-(N,N-disubstituted amino)alkane compound comprising the steps of:

contacting a tertiary aminoalkanol wherein the hydroxy moiety is either primary or secondary of the formula

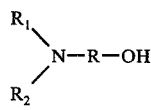

wherein R is a normal or branched chain alkylene radical of from 2 to 10 carbon atoms and, $R_1$ and $R_2$, independently, are straight or branched chain alkyl radicals of from 1 to 18 carbon atoms, or $R_1$ and $R_2$, taken together with the nitrogen atom to which each is attached, form a 4 or 5 membered heterocyclic ring; and a secondary amine of the formula

wherein $R_3$ and $R_4$ are defined as $R_1$ and $R_2$ above, in the presence of a catalytically effective amout of aluminum phosphate having phosphorus content of from about 20 to about 30 wt. % and a surface area of from about 20 m$^2$/g to about 50 M$^2$/g at a temperature of from about 240° C to 320° C under a pressure sufficient to maintain the mixture substantiall in liquid phase; and recovering from the resultant reaction mixture said di-(N,N-substituted amino)alkane compound.

2. The process according to claim 1 wherein said aluminum phosphate has a phosphorus content of from about 23 to about 27 wt. % and a surface area of about 33 m$^2$/g.

3. The process of claim 1 wherein said aluminum phosphate catalyst is prepared by first dissolving an alumina hydrate in excess phosphoric acid to form an acidic solution, neutralizing the solution with a base to form a precipitate; and calcining the precipitate to yield the aluminum phosphate catalyst.

4. The process of claim 1 wherein said tertiary aminoalkanol is a N-(hydroxyalkyl)morpholine of the formula

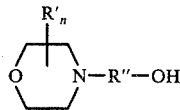

wherein R″ is a straight chain or a branched alkyl radical of from 2 to 4 carbon atoms, R′ is a lower alkyl radical of from 1 to 4 carbon atoms and n is an integer from 0 to 4.

5. The process according to claim 2 wherein said contacting is carried out at a temperature of from about 260° C to about 300° C.

6. The process according to claim 5 wherein the aluminum phosphate catalyst has a phosphorus content of about 25 wt. %.

7. The process according to claim 6 wherein said contacting is effected at a pressure of from about 100 to about 500 psig and wherein water is continuously removed from the reaction zone as a vapor as it is formed in the condensation reaction.

8. The process according to claim 7 wherein said contacting is carried out at a temperature of from about 270° C to about 300° C.

9. The process according to claim 8 wherein said tertiary aminoalkanol is N-(hydroxyalkyl)morpholine and wherein said secondary amine is an N,N-(dialkyl)amine.

10. The process according to claim 8 wherein said tertiary aminoalkanol is N-(hydroxyalkyl)morpholine and said secondary amine is morpholine.

11. The process according to claim 10 wherein said N-(hydroxyalkyl)morpholine is N-(2-hydroxyethyl)morpholine.

12. The process of claim 1 wherein R contains from 2 to 4 carbon atoms; $R_1$, $R_2$, $R_3$ and $R_4$ are independently alkyl of from 1 to 4 carbon atoms; or $R_1$ and $R_2$ together with the nitrogen atom to which they are attached, or $R_3$ and $R_4$ together with the nitrogen to which they are attached, form a morpholine ring or a C-(lower alkyl substituted) morpholine ring.

13. A process for producing a di-(N,N-disubstituted amino)alkane compound comprising the steps of:

contacting an N-(hydroxyalkyl)morpholine compound having the formula:

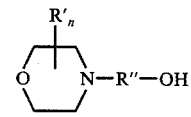

wherein R″ is a straight chain or a branched chain alkyl radical of from 2 to about 10 carbon atoms, R′ is a lower alkyl radical, and n is an integer from 0 to 4, with a morpholine compound of the formula:

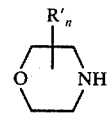

wherein R′ and n are defined as hereinabove in the presence of a catalytically effective amount of an aluminum phosphate having phosphorus content of from about 20 to about 30 wt. % and a surface area of from about 20 m$^2$/g to about 50 m$^2$/g at a temperature of from about 240° C to about 320° C under a pressure sufficient to maintain the mixture substantially in liquid phase; and recovering said di-(N,N-disubstituted amino) alkane compound from the resulting reaction mixture.

* * * * *